US012506301B2

(12) United States Patent
Tegg et al.

(10) Patent No.: US 12,506,301 B2
(45) Date of Patent: Dec. 23, 2025

(54) ELECTRICAL CONNECTOR

(71) Applicant: St. Jude Medical, Cardiology Division, Inc., St. Paul, MN (US)

(72) Inventors: Troy Tegg, Elk River, MN (US); Isaac Remer, Richfield, MN (US); Derek Sutermeister, Ham Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 315 days.

(21) Appl. No.: 18/034,001

(22) PCT Filed: Oct. 29, 2021

(86) PCT No.: PCT/US2021/057176

§ 371 (c)(1),
(2) Date: Apr. 26, 2023

(87) PCT Pub. No.: WO2022/098563

PCT Pub. Date: May 12, 2022

(65) Prior Publication Data

US 2024/0006815 A1 Jan. 4, 2024

Related U.S. Application Data

(60) Provisional application No. 63/110,024, filed on Nov. 5, 2020.

(51) Int. Cl.
*H01R 13/631* (2006.01)
*A61B 18/14* (2006.01)
*A61B 18/00* (2006.01)

(52) U.S. Cl.
CPC ....... *H01R 13/631* (2013.01); *A61B 18/1492* (2013.01); *A61B 2018/00178* (2013.01)

(58) Field of Classification Search
CPC .. H01R 13/631; H01R 13/10; H01R 2201/12; H01R 13/04; A61B 18/1492;
(Continued)

(56) References Cited

U.S. PATENT DOCUMENTS 3,783,440 A 1/1974 Kaurbe et al.
5,104,253 A 4/1992 Zielinski et al.
(Continued)

FOREIGN PATENT DOCUMENTS

WO 2020/168214 A1 8/2020

OTHER PUBLICATIONS

International Search Report and Written Opinion of the International Searching Authority for International Application No. PCT/US2021/057176 dated May 5, 2022.

*Primary Examiner* — Abdullah A Riyami
*Assistant Examiner* — Nader J Alhawamdeh
(74) *Attorney, Agent, or Firm* — Wiley Rein LLP

(57) ABSTRACT

An electrical connector includes a plug portion and a receptacle portion. The plug portion includes a plurality of conductive pins, with a portion of each conductive pin surrounded by a non-conductive post. The receptacle portion includes a plurality of conductive pins recessed into a corresponding plurality of recesses within the receptacle portion. When the plug portion is mated to the receptacle portion, the conductive pins of the plug portion are received within the recesses of the receptacle portion and electrically connected to the conductive pins of the receptacle portion. To advantageously increase creepage and clearance between pins, it is desirable for each recess to have a depth sufficient to receive both a conductive pin and a corresponding surrounding non-conductive post when the plug portion is mated to the receptacle portion.

15 Claims, 4 Drawing Sheets

(58) Field of Classification Search
CPC ........... A61B 2018/00178; A61B 2018/00613; A61N 1/327
See application file for complete search history.

(56) References Cited

U.S. PATENT DOCUMENTS

| | | | | |
|---|---|---|---|---|
| 6,638,088 | B1 | 10/2003 | Richardson | |
| 8,845,368 | B1 | 9/2014 | Gardner | |
| 8,936,484 | B2 | 1/2015 | Metzler et al. | |
| 10,283,887 | B2 * | 5/2019 | Tegg | A61B 18/1492 |
| 2014/0039302 | A1 * | 2/2014 | Miller | H01R 24/86 361/752 |
| 2015/0180150 | A1 | 6/2015 | Shinder-Lerner et al. | |
| 2018/0138619 | A1 * | 5/2018 | Tegg | A61B 18/1492 |
| 2018/0183179 | A1 * | 6/2018 | Byrd | A61M 39/1055 |
| 2019/0393648 | A9 * | 12/2019 | Byrd | A61M 25/0136 |
| 2020/0405387 | A1 | 12/2020 | Wittkampf et al. | |
| 2024/0006815 | A1 * | 1/2024 | Tegg | A61B 18/1492 |

* cited by examiner

ELECTRICAL CONNECTOR

CROSS-REFERENCE TO RELATED APPLICATIONS

This application claims the benefit of U.S. provisional application No. 63/110,024, filed 5 Nov. 2020, which is hereby incorporated by reference as though fully set forth herein.

BACKGROUND

The present disclosure relates generally to electrophysiology catheters. In particular, the present disclosure relates to an electrical connector such as may be used to connect an electrophysiology catheter to electrophysiology system electronics (e.g., high voltage sources).

Ablation therapy may be used to treat various conditions afflicting the human anatomy. One such condition in which ablation therapy may be used is the treatment of cardiac arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmias can create a variety of dangerous conditions including loss of synchronous atrioventricular contractions and stasis of blood flow. It is believed that the primary cause of atrial arrhythmias is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that may lead to arrhythmias.

Electroporation is a non-thermal ablation technique that involves applying strong electric fields that induce pore formation in the cellular membrane. The electric field may be induced by applying a relatively short duration pulse which may last, for example, from a nanosecond to several milliseconds. Such a pulse may be repeated to form a pulse train. When such an electric field is applied to tissue in an in vivo setting, the cells in the tissue are subjected to a trans-membrane potential, which opens the pores on the cell wall. Electroporation may be reversible (i.e., the temporarily-opened pores will reseal) or irreversible (i.e., the pores will remain open, causing cellular destruction). For example, in the field of gene therapy, reversible electroporation is used to transfect high molecular weight therapeutic vectors into the cells. In other therapeutic applications, a suitably configured pulse train alone may be used to cause cell destruction, for instance by causing irreversible electroporation (IRE).

The electrodes used for electroporation therapy may be powered either collectively, in groups, or individually. To fire electrodes either individually or in groups, however, requires that the electrodes be isolated from each other, such that the firing electrode(s) can be maintained at the appropriate high voltage while surrounding electrodes remain at zero volts. Indeed, from both a performance standpoint and a safety standpoint, both creepage and clearance isolation should be present.

Extant electrical connectors, however, either provide isolation between groups of electrodes or no isolation at all.

Without isolation, the therapy applied may be less effective (e.g., because the high voltage intended to be applied by a single electrode is instead reduced and spread over multiple electrodes).

BRIEF SUMMARY

Disclosed herein is an electrical connector for a catheter. The electrical connector includes a plug portion, which includes: a plug body; a plurality of hollow posts extending from the plug body, wherein the plurality of hollow posts are electrically insulative; and a plurality of electrically conductive pins, wherein a first portion of each electrically conductive pin of the plurality of electrically conductive pins is disposed within a respective hollow post of the plurality of hollow posts and a second portion of each electrically conductive pin of the plurality of electrically conductive pins extends out of the respective hollow post of the plurality of hollow posts. The electrical connector further includes a receptacle portion, which in turn includes: a receptacle body, wherein the receptacle body is electrically insulative; a plurality of holes formed in the receptacle body; and a plurality of electrically conductive pins recessed within the plurality of holes.

The plurality of hollow posts may be integrally formed with the plug body.

The plurality of hollow posts and the plurality of electrically conductive pins can be arranged on the plug body in a first array and the plurality of holes and the plurality of electrically conductive pins can be arranged on the receptacle body in a second array complementary to the first array.

It is also contemplated that each electrically conductive pin of the plurality of conductive pins recessed within the plurality of holes can have a hollow portion configured to receive a corresponding electrically conductive pin of the plurality of electrically conductive pins of the plug portion.

According to embodiments of the disclosure, when the plug portion is inserted into the receptacle portion, each electrically conductive pin of the plug portion is inserted within a corresponding hole of the plurality of holes to an extent sufficient to electrically conductively couple with an electrically conductive pin of the plurality of electrically conductive pins respectively recessed within the corresponding hole of the plurality of holes. In further embodiments, each of the plurality of holes has a depth sufficient to receive at least a portion of a corresponding hollow post of the plurality of hollow posts when the plug portion is inserted into the receptacle portion.

In further embodiments, the electrical connector may also include a plurality of alignment pegs extending from the plug body; and a plurality of alignment holes, configured to receive the plurality of alignment pegs, formed in the receptacle body.

In still further embodiments, the electrical connector may also include a first mating component on the plug body; and a second mating component, complementary to the first mating component, on the receptacle body. For instance, one of the first mating component and the second mating component may include a tab or barb and another of the first mating component and the second mating component may include a slot or aperture complementary to the tab or barb.

Also disclosed herein is an electrical connector, including: a plug portion including a plurality of conductive pins, wherein a portion of each conductive pin is surrounded by a non-conductive post; and a receptacle portion including a plurality of conductive pins recessed into a corresponding plurality of recesses within the receptacle portion, wherein, when the plug portion is mated to the receptacle portion, the plurality of conductive pins of the plug portion are received within the plurality of recesses of the receptacle portion and electrically connected to the plurality of conductive pins of the receptacle portion.

According to aspects of the disclosure, each recess of the plurality of recesses has a depth sufficient to receive both a conductive pin and a corresponding surrounding non-conductive post of the plug portion when the plug portion is mated to the receptacle portion. In further aspects of the disclosure, the plurality of conductive pins of the receptacle portion can be hollow to receive the plurality of conductive pins of the plug portion therein when the plug portion is mated to the receptacle portion.

The non-conductive post can be integrally formed with the plug portion.

It is contemplated that the plurality of conductive pins of the plug portion and the plurality of conductive pins of the receptacle portion can be arranged in complementary arrays.

Optionally, the plug portion can include a first mating component and the receptacle portion can include a second mating component complementary to the first mating component. For example, one of the first mating component and the second mating component may be a tab or barb and another of the first mating component and the second mating component may be a slot or aperture complementary to the tab or barb.

In still other embodiments, the plug portion can include an alignment post and the receptacle portion further can include an alignment recess configured to receive the alignment post when the plug portion is mated to the receptacle portion.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

Aspects of the instant disclosure relate to electrical connectors. Although embodiments of the disclosure will be described in connection with electrical connectors utilized to connect electrophysiology catheters to associated electronics in an electroporation therapy system, those of ordinary skill in the art will appreciate that the teachings herein can be applied to good advantage in other contexts as well.

Figure 1A:
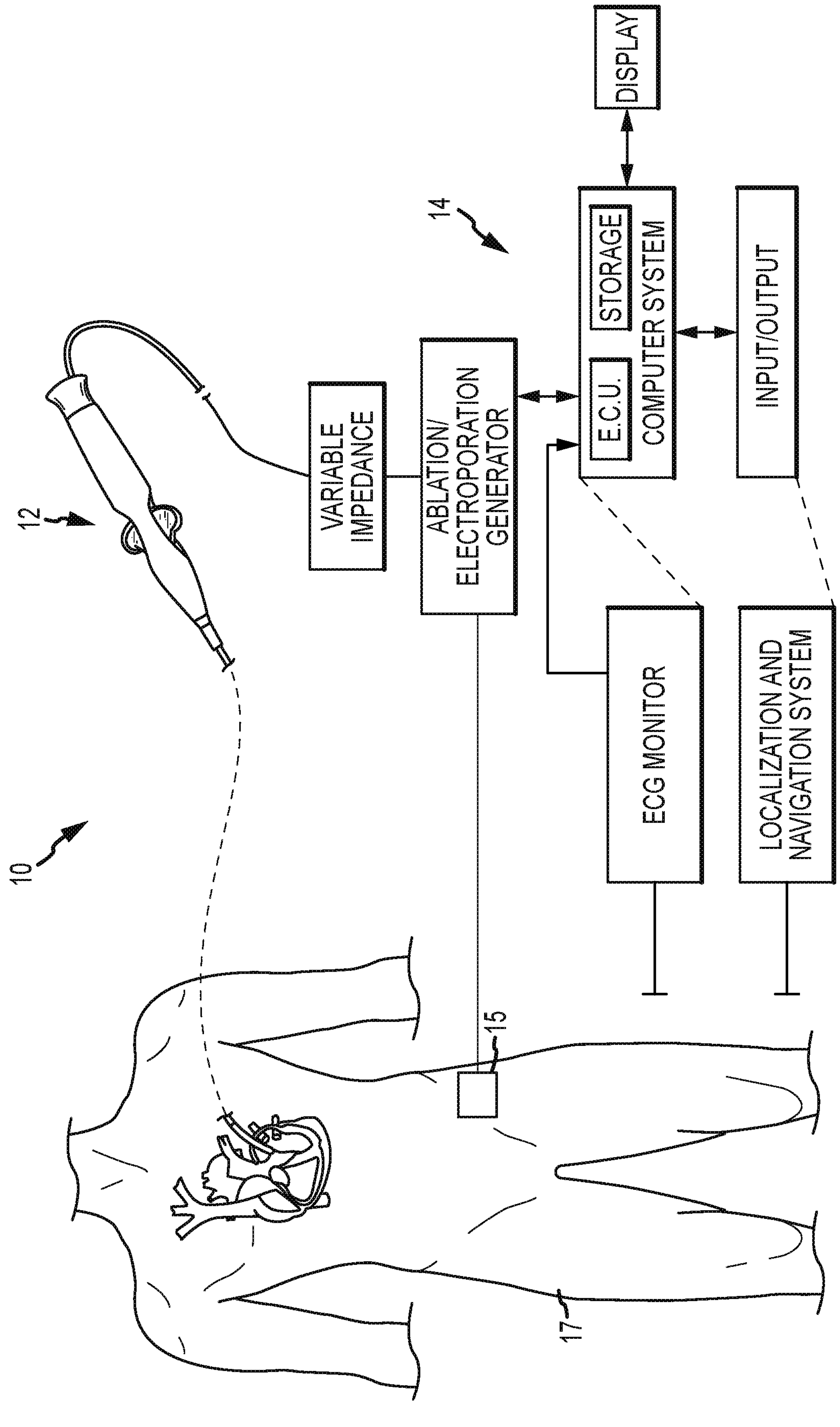
FIG. 1A is a diagrammatic and block diagram view of an illustrative system for electroporation therapy.

FIG. 1A is a diagrammatic and block diagram view of a system 10 for electroporation therapy. In general, the various embodiments include an electrode assembly disposed at the distal end of a catheter 12. As used herein, "proximal" refers to a direction toward the end of the catheter near the clinician, and "distal" refers to a direction away from the clinician and (generally) inside the body of a patient 17. The electrode assembly includes one or more individual, electrically-isolated electrode elements. Each electrode element, also referred to herein as a catheter electrode, is individually wired such that it can be selectively paired or combined with any other electrode element to act as a bipolar or multi-polar electrode.

System 10 may be used for irreversible electroporation to destroy tissue. In particular, system 10 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field (i.e., pulsed field ablation (PFA)) in the form of short-duration pulses (e.g., about 0.1 ms to about 20 ms duration) between closely-spaced electrodes capable of delivering an electric field strength of about 0.1 kV/cm to about 1.0 kV/cm. As described, for example, in international application publication WO2019173309A1, which is hereby incorporated by reference as though fully set forth herein, system 10 may be used with a high-output hoop catheter for high output (e.g., high voltage and/or high current) electroporation procedures.

Figure 1B:
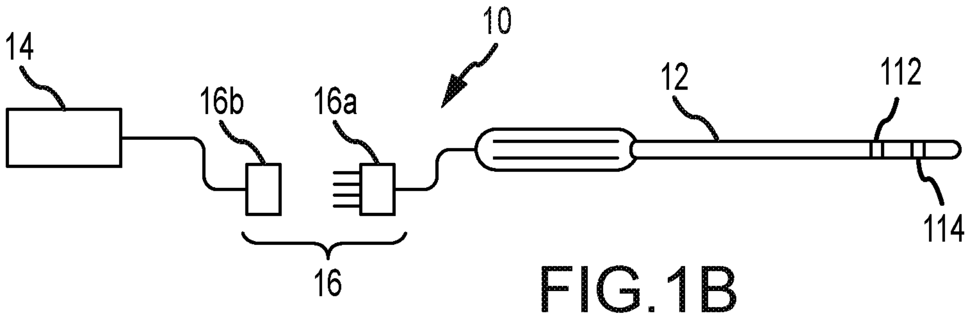
FIG. 1B is a schematic representation of a catheter for use in connection with the illustrative electroporation system of FIG. 1A.

FIG. 1B schematically illustrates catheter 12 as connected to electronics 14 within system 10. As those of ordinary skill in the art will appreciate, and as shown in FIG. 1A, electronics 14 may include an ablation/electroporation generator, an electroanatomical mapping system, a computer system, a display, and the like.

Catheter 12 may also include thereon one or more electrodes 112, 114 (collectively referred to herein as an "electrode assembly"), which may be used for a variety of diagnostic and/or therapeutic purposes including, without limitation, cardiac mapping and/or ablation (e.g., IRE ablation). For example, and in some embodiments, the electrode assembly may be configured as a bipolar electrode assembly for use in bipolar-based electroporation therapy. Specifically, electrodes 112, 114 may be individually electrically coupled to generator 14 (e.g., via suitable electrical wire or other suitable electrical conductors connected through electrical connector 16 as discussed in further detail herein) and are configured to be selectively energized (e.g., by an electroporation generator 14 and/or an associated computer system) with opposite polarities to generate a potential and corresponding electric field therebetween for IRE therapy. That is, one of electrodes 112, 114 can be configured to function as a cathode, and the other can be configured to function as an anode.

Electrodes 112, 114 may be any suitable electroporation electrodes. In an exemplary embodiment, electrodes 112, 114 are ring electrodes, though electrodes 112, 114 may have any other shape or configuration. It is realized that the shape, size, and/or configuration of electrodes 112, 114 may impact various parameters of the applied electroporation therapy. For example, increasing the surface area of one or both electrodes 112, 114 may reduce the applied voltage needed to cause the same level of tissue destruction.

Moreover, although each of electrode 112 and electrode 114 are illustrated as single electrodes, either or both of electrode 112 and electrode 114 may be alternatively embodied as two or more discrete electrodes.

Further, while the electrode assembly is described as a bipolar electrode assembly, it should be understood that in some embodiments, the electrode assembly may be configured as a monopolar electrode assembly and use a patch electrode on the patient's skin (e.g., 15) as a return or indifferent electrode.

Also shown in FIG. 1 is an electrical connector 16, including a plug portion 16*a* and a receptacle portion 16*b*, embodiments of which are described in detail below. As shown, plug portion 16*a* is connected to catheter 12, while receptacle portion 16*b* is connected to electronics 14, but this arrangement could be reversed without departing from the spirit and scope of the instant disclosure. The ordinarily skilled artisan will appreciate that, when plug portion 16*a* is mated to receptacle portion 16*b*, catheter 12 becomes electrically coupled to electronics 14, enabling power, data, and other electrical signals to pass between the two. In particular, and as mentioned above, electrical connector 16 permits each individual electrode on catheter 12 to be individually and selectively paired or combined with any other electrode (or electrodes) to act as a bipolar or multi-polar electrode.

Figure 2A:
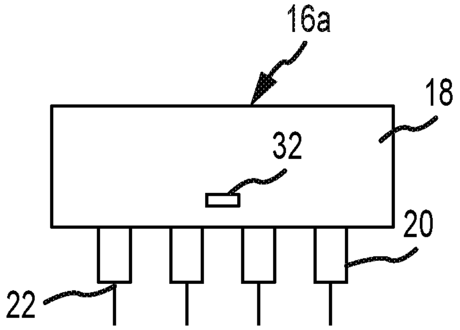
FIG. 2A is a top view of a plug portion of an electrical connector according to embodiments of the instant disclosure.
Figure 2B:
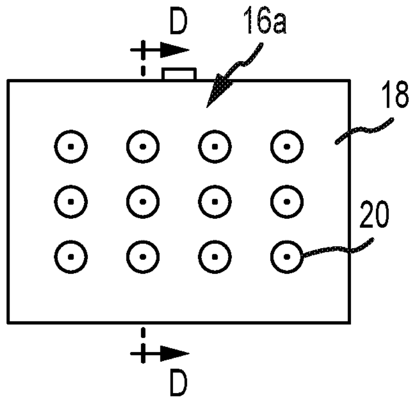
FIG. 2B is a front view of the plug portion shown in FIG. 2A.
Figure 2C:
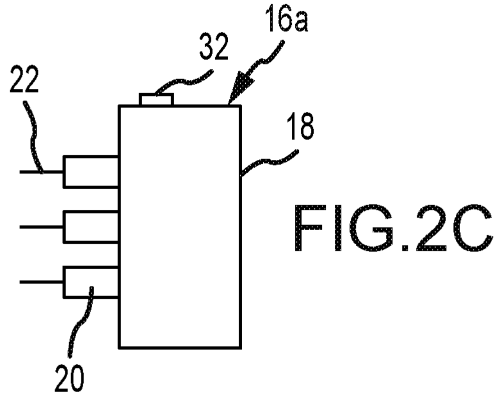
FIG. 2C is a side view of the plug portion shown in FIG. 2A.
Figure 2D:
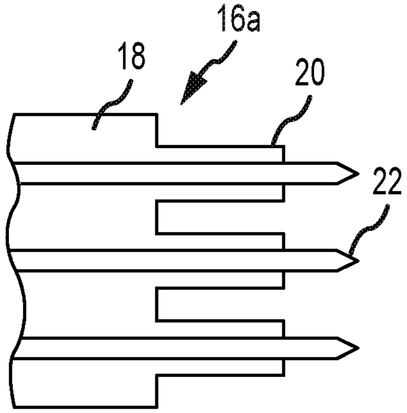
FIG. 2D is a cross-section of the plug portion taken along line D-D in FIG. 2B.

FIGS. 2A, 2B, and 2C are, respectively, top, front, and side views of plug portion 16*a*. FIG. 2D is a cross-sectional view of plug portion 16*a* taken along line D-D. As shown to good advantage in FIGS. 2A-2D, plug portion 16*a* includes a plug body 18 and a plurality of hollow posts 20 extending therefrom. In embodiments of the disclosure, hollow posts 20 are integrally formed with plug body 18, such as by molding plug body 18 and hollow posts 20 as a unitary assembly. Further, hollow posts 20 are electrically insulative; plug body 18 may also be electrically insulative.

A corresponding plurality of conductive pins 22 extend from plug portion 16*a*. More particularly, a first portion of each conductive pin 22 is disposed within a hollow post 20, while a second portion of each conductive pin 22 extends out of the hollow post 20.

FIGS. 2A-2D depict a total of twelve hollow posts 20 and corresponding conductive pins 22, arranged in a four-by-three array. It should be understood, however, that this configuration is merely exemplary and that any number of hollow posts 20 and conductive pins 22, in any arrangement, are contemplated within the instant disclosure depending upon the specific application and/or needs associated with catheter 12 and/or electronics 14.

Figure 3A:
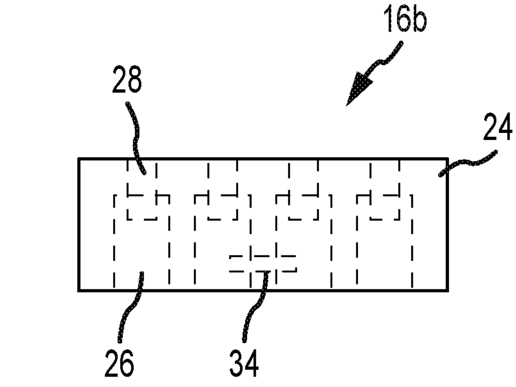
FIG. 3A is a top view of a receptacle portion of an electrical connector according to embodiments of the instant disclosure.
Figure 3B:
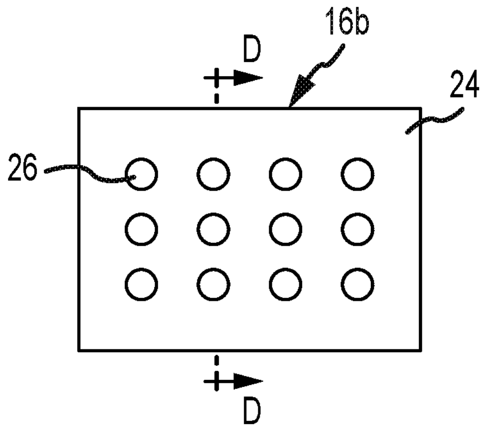
FIG. 3B is a front view of the receptacle portion shown in FIG. 3A.
Figure 3C:
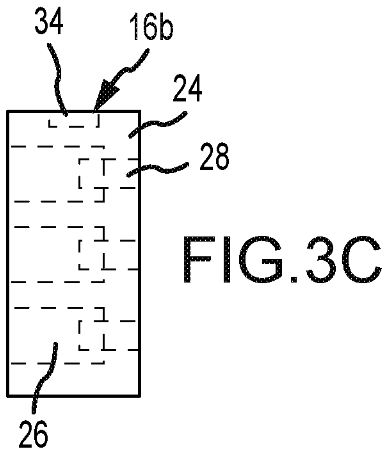
FIG. 3C is a side view of the receptacle portion shown in FIG. 3A.
Figure 3D:
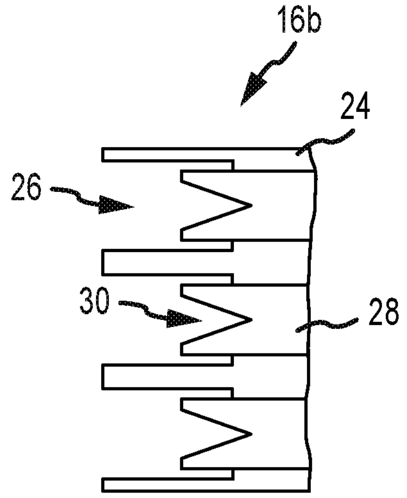
FIG. 3D is a cross-section of the receptacle portion taken along line D-D in FIG. 3B.

FIGS. 3A, 3B, and 3C are, respectively, top, front, and side views of receptacle portion 16*b*. FIG. 3D is a cross-sectional view of receptacle portion 16*b* taken along line D-D. As shown to good advantage in FIGS. 3A-3D, receptacle portion 16*b* includes a receptacle body 24 with a plurality of holes or recesses 26 formed therein. Like hollow posts 20 and plug body 18, receptacle body 24 is electrically insulative.

Within each hole 26 is an electrically conductive pin 28. In embodiments of the disclosure, each conductive pin 28 includes a hollow portion 30.

FIGS. 3A-3D depict a total of twelve recesses 26 and corresponding conductive pins 28, arranged in a four-by-three array. It should be understood, however, that this configuration is merely exemplary and that any number of recesses 26 and conductive pins 28, in any arrangement, are contemplated within the instant disclosure depending upon the specific application and/or needs associated with catheter 12 and/or electronics 14.

Figure 4:
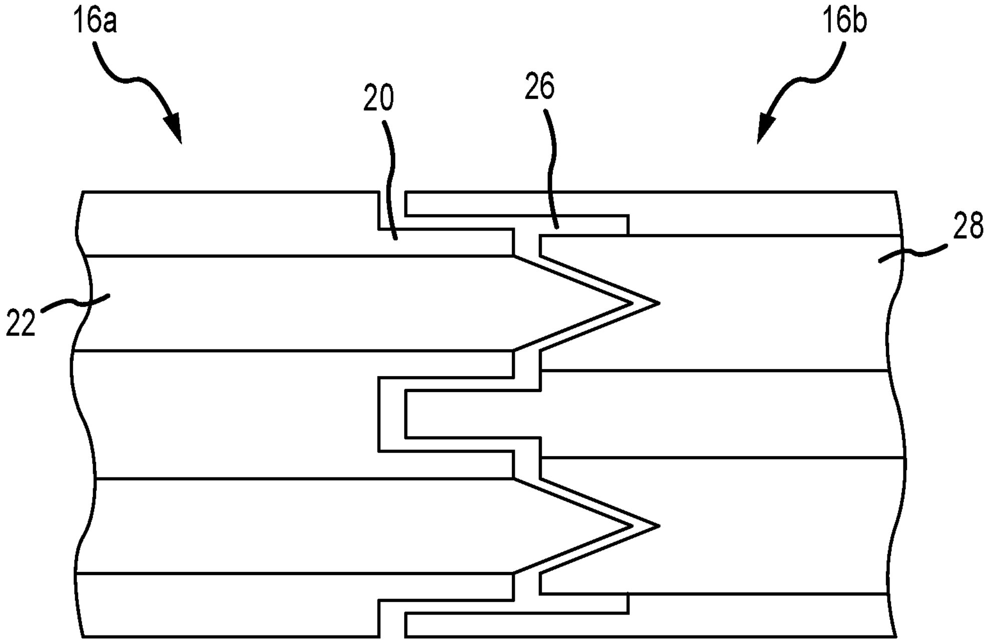
FIG. 4 depicts a plug portion mated to a receptacle portion.

Of course, those of ordinary skill in the art will appreciate that, because plug portion 16*a* is designed to mate to receptacle portion 16*b*, there will often be one-to-one correspondence between the configuration of posts 20 and pins 22 on plug portion 16*a* and the configuration of recesses 26 and pins 28 on receptacle portion 16*b* (that is, the two will be complementary to each other). In this regard, FIG. 4 illustrates a portion of electrical connector 16 when plug portion 16*a* is mated to receptacle portion 16*b*. As shown in FIG. 4, pins 22 of plug portion 16*a* are received into respective hollow portions 30 of pins 28 on receptacle portion 16*b*, thus conductively coupling pins 22 to pins 28.

FIG. 4 illustrates that posts 20 are also received within recesses 26. This advantageously increases creepage between adjacent pins; in embodiments of the disclosure, creepage may be increased by a factor of about six or more relative to extant connectors, which helps ensure electrical isolation between individual pins. This, in turn, can advantageously allow pins to be used in multiple configurations and polarity settings (e.g., adjusted via controls on an ablation generator), and also allow for higher voltage differentials between operating pins. It may also allow for a reduction in the total number of pins required for a given number of electrodes on catheter 12.

Clearance is also advantageously increased by approximately the same factor because, once plug portion 16*a* is mated to receptacle portion 16*b*, the clearance path and creepage path are substantially the same.

Indeed, those of ordinary skill in the art will appreciate that, the further plug portion 16*a* is inserted into receptacle portion 16*b* (e.g., the further pins 22 of plug portion 16*a* are inserted into pins 28 of receptacle portion 16*b*), the greater the order of magnitude increase in both creepage and clearance.

To aid alignment between plug portion 16*a* and receptacle portion 16*b*, plug portion 16*a* and receptacle portion 16*b* can include complementary alignment pegs and alignment holes configured to receive the pegs formed in their respective bodies. In embodiments of the disclosure, these alignment pegs and alignment holes can resemble posts 20 and recesses 26 without conductive pins disposed therein. In other embodiments of the disclosure, these alignment pegs and alignment holes can be dedicated structures, and may be uniquely shaped (e.g., with limited or no axes of symmetry) to ensure a correct orientation between plug portion 16*a* and receptacle portion 16*b*. For instance, a T-shaped alignment post could be provided on plug body 18, while a complementary T-shaped alignment hole could be formed within receptacle body 24.

Similarly, electrical connector 16 can include mating components to enhance the security of the connection between plug body 18 and receptacle body 24 when plug portion 16*a* is mated to receptacle portion 16*b*. For instance, one or more tabs 32 on plug body 18 can fit into corresponding slots or apertures 34 on receptacle body 24. In aspects of the disclosure, tabs 32 can include barbs to make it more difficult to remove tabs 32 from slots 34.

Although several embodiments have been described above with a certain degree of particularity, those skilled in the art could make numerous alterations to the disclosed embodiments without departing from the spirit or scope of this invention.

For example, although plug portion **16*a* and receptacle portion 16*b*** are shown as rectangular components, with their respective conductive pins and recesses arranged in rectangular arrays, this shape is merely exemplary, and other shapes and array configurations are regarded as within the scope of the instant disclosure.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrical connector for a catheter, comprising:
- a plug portion comprising:
  - a plug body;
  - a first mating component on the plug body;
  - a plurality of hollow posts extending from the plug body, wherein the plurality of hollow posts are electrically insulative; and
  - a plurality of electrically conductive pins, wherein a first portion of each electrically conductive pin of the plurality of electrically conductive pins is disposed within a respective hollow post of the plurality of hollow posts and a second portion of each electrically conductive pin of the plurality of electrically conductive pins extends out of the respective hollow post of the plurality of hollow posts; and
- a receptacle portion comprising:
  - a receptacle body, wherein the receptacle body is electrically insulative;
  - a second mating component, complementary to the first mating component, on the receptacle body;
  - a plurality of holes formed in the receptacle body; and
  - a plurality of electrically conductive pins recessed within the plurality of holes,
- wherein one of the first mating component and the second mating component comprises a tab and another of the first mating component and the second mating component comprises a slot complementary to the tab.

2. The electrical connector according to claim 1, wherein the plurality of hollow posts are integrally formed with the plug body.

3. The electrical connector according to claim 1, wherein the plurality of hollow posts and the plurality of electrically conductive pins are arranged on the plug body in a first array, wherein the plurality of holes and the plurality of electrically conductive pins are arranged on the receptacle body in a second array, and wherein the second array is complementary to the first array.

4. The electrical connector according to claim 1, wherein each electrically conductive pin of the plurality of conductive pins recessed within the plurality of holes has a hollow portion configured to receive a corresponding electrically conductive pin of the plurality of electrically conductive pins of the plug portion.

5. The electrical connector according to claim 1, wherein, when the plug portion is inserted into the receptacle portion, each electrically conductive pin of the plug portion is inserted within a corresponding hole of the plurality of holes to an extent sufficient to electrically conductively couple with an electrically conductive pin of the plurality of electrically conductive pins respectively recessed within the corresponding hole of the plurality of holes.

6. The electrical connector according to claim 1, wherein each of the plurality of holes has a depth sufficient to receive at least a portion of a corresponding hollow post of the plurality of hollow posts when the plug portion is inserted into the receptacle portion.

7. The electrical connector according to claim 1, further comprising:
- a plurality of alignment pegs extending from the plug body; and
- a plurality of alignment holes, configured to receive the plurality of alignment pegs, formed in the receptacle body.

8. An electrical connector comprising:
- a plug portion including a plurality of conductive pins, wherein a portion of each conductive pin is surrounded by a non-conductive post, and wherein the plug portion further comprises a first mating component; and
- a receptacle portion including a plurality of conductive pins recessed into a corresponding plurality of recesses within the receptacle portion, and wherein the receptacle portion further comprises a second mating component complementary to the first mating component,
- wherein one of the first mating component and the second mating component comprises a tab and another of the first mating component and the second mating component comprises a slot complementary to the tab, and
- wherein, when the plug portion is mated to the receptacle portion, the plurality of conductive pins of the plug portion are received within the plurality of recesses of the receptacle portion and electrically connected to the plurality of conductive pins of the receptacle portion.

9. The electrical connector according to claim 8, wherein each recess of the plurality of recesses has a depth sufficient to receive both a conductive pin and a corresponding surrounding non-conductive post of the plug portion when the plug portion is mated to the receptacle portion.

10. The electrical connector according to claim 8, wherein the plurality of conductive pins of the receptacle portion are hollow to receive the plurality of conductive pins of the plug portion therein when the plug portion is mated to the receptacle portion.

11. The electrical connector according to claim 8, wherein the non-conductive post is integrally formed with the plug portion.

12. The electrical connector according to claim 8, wherein the plurality of conductive pins of the plug portion and the plurality of conductive pins of the receptacle portion are arranged in complementary arrays.

13. The electrical connector according to claim 8, wherein the plug portion further comprises an alignment post and the receptacle portion further comprises an alignment recess configured to receive the alignment post when the plug portion is mated to the receptacle portion.

14. An electrical connector for a catheter, comprising:

a plug portion comprising:

a plug body;

a first mating component on the plug body;

a plurality of hollow posts extending from the plug body, wherein the plurality of hollow posts are electrically insulative; and a plurality of electrically conductive pins, wherein a first portion of each electrically conductive pin of the plurality of electrically conductive pins is disposed within a respective hollow post of the plurality of hollow posts and a second portion of each electrically conductive pin of the plurality of electrically conductive pins extends out of the respective hollow post of the plurality of hollow posts; and a receptacle portion comprising:

a receptacle body, wherein the receptacle body is electrically insulative;

a second mating component, complementary to the first mating component, on the receptacle body;

a plurality of holes formed in the receptacle body; and a plurality of electrically conductive pins recessed within the plurality of holes, wherein one of the first mating component and the second mating component comprises a barb and another of the first mating component and the second mating component comprises an aperture to receive the barb.

15. An electrical connector comprising:

a plug portion including a plurality of conductive pins, wherein a portion of each conductive pin is surrounded by a non-conductive post, and wherein the plug portion further comprises a first mating component; and a receptacle portion including a plurality of conductive pins recessed into a corresponding plurality of recesses within the receptacle portion, and wherein the receptacle portion further comprises a second mating component complementary to the first mating component, wherein one of the first mating component and the second mating component comprises a barb and another of the first mating component and the second mating component comprises an aperture to receive the barb, and wherein, when the plug portion is mated to the receptacle portion, the plurality of conductive pins of the plug portion are received within the plurality of recesses of the receptacle portion and electrically connected to the plurality of conductive pins of the receptacle portion.

* * * * *